United States Patent [19]

Hollis et al.

[11] Patent Number: 5,250,194
[45] Date of Patent: Oct. 5, 1993

[54] N-DODECYL HETEROCYCLIC COMPOUNDS USEFUL AS INDUSTRIAL MICROBICIDES AND PRESERVATIVES

[75] Inventors: C. George Hollis; S. Rao Rayudu; Marilyn S. Whittemore, all of Germantown, Tenn.

[73] Assignee: Buckman Laboratories International, Inc., Memphis, Tenn.

[21] Appl. No.: 908,555

[22] Filed: Jun. 30, 1992

Related U.S. Application Data

[63] Continuation of Ser. No. 654,492, Feb. 13, 1991, abandoned.

[51] Int. Cl.$^5$ .................................................. C02F 1/50
[52] U.S. Cl. .................................... 210/764; 162/161; 514/183; 514/231.2; 514/315; 514/359; 514/396; 514/408; 514/424
[58] Field of Search ............... 210/698, 764, 916, 928; 162/161; 514/183, 231.2, 315, 359, 396, 408, 424

[56] References Cited

U.S. PATENT DOCUMENTS

| 2,881,070 | 4/1959 | Pera | 92/3 |
| 3,686,399 | 8/1972 | Sanne et al. | 514/231.2 |
| 3,919,422 | 11/1975 | Huber | 514/226.8 |
| 4,762,522 | 8/1988 | Maue | 8/94.21 |
| 4,945,109 | 7/1990 | Rayudu | 514/478 |

FOREIGN PATENT DOCUMENTS

| 614214 | 8/1962 | Belgium . | |
| 0055991 | 7/1982 | European Pat. Off. | 514/231.2 |
| 0142799 | 5/1985 | European Pat. Off. | 514/231.2 |
| 299814 | 5/1992 | German Democratic Rep. . | |
| 1364312 | 8/1974 | United Kingdom . | |

OTHER PUBLICATIONS

Koch et al., "The Algicidal Action of Chemical Substances" Nachrichtenbl. Deutsch. Pflazenshutzd. 25:37-38 (1973).

Chemical Abstracts No. 117:126446c, Issue 21 (1992) Andreas et al., "Synergistic Fungicidal Compositions Comprising Morpholine Derivatives".

R. A. Firestone, et al., Proc. Int. Symposium, vol. 2, 1990, pp. 1455-1464.

Raymond A. Firestone, et al., J. Med. Chem., vol. 30, 1987, pp. 1519-1521.

E. Ian Mercer, Biochemical Society Transactions, vol. 19, pp. 788-792.

Raymond A. Firestone, et al., Journal of Medicinal Chemistry, vol. 25, No. 5, 1982, pp. 539-544.

Raymond A. Firestone, et al., Journal of Mecidinal Chemistry, vol. 22, No. 9, 1979, pp. 1130-1133.

Von Wolfgang Koch, Nachrichtenbl. Deutseh. Pflazenschutzd. vol. 25, 1973, pp. 37-40.

G. Matolcsy, et al., Research Institute for Plant, Budapest, vol. 49, No. 2, 1979, pp. 325-331.

K. Baggaley et al., Biochem Pharmacol. vol. 24, No. 20, pp. 1902-1903, 1975 (abstract only).

C. Wilkinson et al., Biochem Pharmacol. vol. 23, No. 17, pp. 2377-2386, 1974 (abstract only).

*Primary Examiner*—Peter Hruskoci
*Attorney, Agent, or Firm*—Finnegan, Henderson, Farabow, Garrett & Dunner

[57] ABSTRACT

A method for inhibiting the growth of microorganisms in which an N-dodecyl heterocyclic compound in an amount effective to inhibit the growth of microorganisms is contacted with an aqueous system susceptible to such growth. N-dodecyl heterocylic compounds are also shown to be useful as microbicides in the inhibition of the formation of slime in aqueous systems or the deterioration or disfigurement of susceptible substances due to microbiological growth. Microbicidal compositions containing an N-dodecyl heterocyclic compound in a non-pharmaceutically acceptable carrier are also described.

25 Claims, No Drawings

N-DODECYL HETEROCYCLIC COMPOUNDS USEFUL AS INDUSTRIAL MICROBICIDES AND PRESERVATIVES

This application is a continuation of U.S. patent application Ser. No. 07/654,492, filed Feb. 13, 1991, now abandoned.

FIELD OF THE INVENTION

The present invention relates to a method of using N-dodecyl heterocyclic compounds for industrial microbicidal and preservative purposes. N-Dodecyl heterocyclic compounds have been found to inhibit, that is reduce or prevent, the growth of microorganisms.

BACKGROUND OF THE INVENTION

A large number of commercial, industrial, agricultural, and wood products are subject to microbiological attack which reduces or destroys their economic value. Examples of materials that may be subject to microbiological degradation are surface coatings, wood, agricultural seed, leather and plastics, including flexible plastics. The temperature at which these products are stored and their intrinsic characteristics make these products susceptible to the growth of microorganisms. These microorganisms can be introduced during the manufacturing of these products by exposure to air, tanks, pipes, equipment, and humans and/or during their use from multiple openings and reclosures of packaged products and by the introduction of contaminated objects to stir or remove material.

Aqueous systems containing organic materials are also highly subject to microbiological attack. Such aqueous systems include latexes, surfactants, dispersants, stabilizers, thickeners, adhesives, starches, waxes, proteins, emulsifying agents, detergents, cellulose products, and resins formulated in aqueous solutions, emulsions or suspensions. These systems frequently contain relatively large amounts of water causing them to be well-suited environments for microbiological growth and thus attack and degradation. Microbiological degradation of aqueous systems containing organic materials may manifest itself as a variety of problems, such as loss of viscosity, gas formation, objectionable odors, decreased pH, emulsion breaking, color change, and gelling.

Another objectionable phenomenon occurring in industrial process systems involving water is slime formation. Slime consists of matted deposits of microorganisms, fibers and debris. It may be stringy, pasty, rubbery, tapioca-like, or hard, and may have a characteristic undesirable odor that is different from that of the liquid suspensions in which it is formed. The microorganisms involved in its formation are primarily different species of spore-forming and nonspore-forming bacteria, particularly capsulated forms of bacteria which secrete gelatinous substances that envelop or encase the cells. Slime microorganisms also include filamentous bacteria, filamentous fungi of the mold type, yeasts, and yeast-like organisms. Slime reduces yields in paper production and causes plugging and other problems in water systems.

Some N-dodecyl heterocyclic compounds are known to have pharmacological uses. For example, N-dodecylmorpholine and N-dodecylimidazole, have been shown to be lysosomotropic detergents which are useful a anti-cancer compounds and spermicides. See R. A. Firestone and J. M. Pisano, "Solution Behavior of Surfactants: Theoretical Applied Aspects" [Proc. Int. Symposium], Meeting Date 1980, Volume 2, 1455-64, edited by Mittal, K. L. and Fendler, Eleaner J. N-Dodecylimidazole has been disclosed to be an inhibitor of cholesterol biosynthesis in rat liver and an inhibitor of epoxidation of aldrin of rat liver. See, respectively, K.H. Baggeley et al., *Biochemical Pharmacology*, 24 (20), 1975, 1902-3 and C.F. Wilkinson et al., *Biochemical Pharmacology*, 23 (17), 1974, 2377-86. N-Dodecylmorpholine has been reported to help the transport of anionic drugs. See N. Barker and J. Hadgraft, *International Journal of Pharmacology*, 8 (3), 193-202. Other pharmacological uses for N-dodecylated heterocyclic compounds have also been mentioned in the literature.

However, the utility and effectiveness of N-dodecyl heterocyclic compounds as industrial microbicides and preservatives has not been known or appreciated in the prior art.

SUMMARY OF THE INVENTION

It is an object of this invention to provide a method for inhibiting the growth of microorganisms in aqueous systems employing N-dodecyl heterocyclic compounds as non-corrosive industrial microbicides.

A second object is to provide a method for inhibiting the formation of slime in an aqueous medium such as industrial cooling water or pulp and paper systems.

A third object of the present invention is to provide a method for inhibiting the growth of microorganisms on a substance susceptible to deterioration or disfigurement by microorganisms.

A fourth object of this invention is to provide a microbicidal composition containing an N-dodecyl heterocyclic compound.

The first object of the present invention is accomplished by a method for inhibiting the growth of microorganisms in an aqueous system comprising the step of contacting an aqueous system susceptible to the growth of microorganisms with an N-dodecyl heterocyclic compound in an amount effective to inhibit the growth of the microorganisms.

The second object is achieved with a method of inhibiting the formation of slime comprising the step of contacting an aqueous system susceptible to the formation of slime with an N-dodecyl heterocyclic compound in an amount effective to inhibit the formation of the slime.

The third object is realized using a method of inhibiting microbiological deterioration or disfigurement comprising the step of contacting a substance susceptible to microbiological deterioration or disfigurement with an N-dodecyl heterocyclic compound in an amount effective to inhibit the growth of microorganisms.

The fourth object is realized by a microbicidal composition comprising an N-dodecyl heterocyclic compound present in an amount effective to inhibit the growth of microorganisms and a non-pharmaceutically acceptable carrier.

Additional objects and advantages of the invention will be set forth in the description which follows, and in part will be apparent from the description, or may be learned by practice of the invention.

DETAILED DESCRIPTION

The N-dodecyl heterocyclic compounds employed in the present invention preferably have the following general formula:

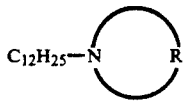

The heterocyclic ring defined by

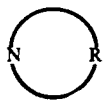

may be a ring having five to ten members and is preferably a five-, six- or seven-membered ring. Although the heterocyclic ring always contains one nitrogen atom, the remainder is generally a carbocycle. However, the ring may contain one or more additional heteroatoms selected from N, O, or S. The ring may be saturated or unsaturated. The ring may also have common substituents such as alkyl groups, substituted alkyl groups, alkenyl groups, substituted akenyl groups, amino groups, an oxo group to form a cyclic ketone, halogens, etc. The heterocyclic ring may also be part of a multiple ring structure.

The following lists illustrate possible heterocyclic ring structures contemplated for the N-dodecyl heterocyclic compounds utilized in a preferred embodiment of the present invention. One of ordinary skill will recognize that other ring structures may also be used in the present invention. The rings may be substituted or unsubstituted as described above. Examples of five-membered heterocyclic rings include: pyrrolidinyl, 2-pyrrolidinonyl, pyrrollinyl, pyrazolidinyl, pyazolinyl, pryazolyl, imidizolidinyl, substituted imidizolidinyl, imidizolinyl, imidazolyl and oxazolinyl. Types of six-membered rings include: piperadinyl, piperazinyl, and morpholinyl. Seven- and eight-membered rings such as hexamethyleneimine and heptamethyleneimine are also usable in the present invention.

The nitrogen-containing heterocycles are available either commercially from laboratory supply houses or can be prepared from readily available starting materials using well-known literature methods.

The following N-dodecyl heterocyclic compounds are preferred in the practice of the present invention and further illustrate preferred heterocyclic groups: N-dodecylmorpholine, N-dodecylimidazole, N-dodecyl-2,6-dimethylmorpholine, N-dodecyl-5-chloromethyl-2-oxazolidinone, N-dodecyl-2-pyrrolidinone, N-dodecylhexamethyleneimine, N-dodecylpyrrolidine, N-dodecyl-3-methylpiperidine, N-dodecylpiperidine, N-dodecyl-4-methylpiperidine and N-dodecyl-2-methylpiperidine. Most preferred of these compounds are N-dodecylmorpholine and N-dodecylimidazole.

The compounds of the present invention are preferably prepared by reacting a nitrogen-containing heterocycle having at least one secondary amino group within the ring structure, i.e. an amino group having a reactive hydrogen atom, obtained as described above, with dodecyl bromide, chloride or iodide, and potassium carbonate, or other suitable base, in the presence of a suitable solvent.

The synthesis of N-dodecyl heterocyclic compounds can generally be carried out in an organic solvent which may be a solvent for at least one of the reactants but which is generally a solvent for the desired product. The temperature at which these reactions can be run preferably varies from ambient to 100° C., more preferably the reaction temperature is between 50 and 70° C. The reactions are generally stirred for 2 to 16 hours, preferably for 6 to 10 hours.

After the reaction is complete, as shown by gas chromatographic analysis, the reaction product can be worked up using well-known techniques to isolate and purify the desired N-dodecyl heterocyclic compound. Excess base and any solids formed during the reaction can be filtered off, and the filtrate evaporated to yield the crude product. The crude product, in most cases, is an oily liquid which can be distilled to yield the pure compound. In case the desired N-dodecyl heterocyclic compound is a solid, it can be recrystallized from an appropriate organic solvent to yield a pure compound. It should be noted, however, that both pure and crude compounds can be used for the purposes of this invention.

The preparation of the N-dodecyl heterocyclic compounds is not limited to the exact process or steps described above. Any equivalent procedure which yields the desired end product may be used.

According to the methods of the present invention, inhibition of the growth of microorganisms includes both the reduction and/or the prevention of such growth.

The N-dodecyl heterocyclic compounds can be used in a method for inhibiting the growth of microorganisms in an aqueous system which comprises contacting the system susceptible to the growth of microorganisms with the N-dodecyl heterocyclic compound in an amount effective to inhibit the growth of the microorganisms. The N-dodecyl heterocyclic compounds are non-corrosive and may be added directly to the system under working conditions. Representative aqueous systems include aqueous solutions, emulsions and suspensions. Specific systems include water-based paints and metalworking fluids.

The present invention also relates to a microbicidal composition comprising an N-dodecyl heterocyclic compound present in an amount effective to inhibit the growth of microorganisms and a non-pharmaceutically acceptable carrier. Non-pharmaceutically acceptable carriers include solvents, surfactants and other carriers used in industrial applications as would be known to those skilled in the art. These non-pharmaceutically acceptable carriers do not have the low toxicity profiles and purity required of pharmaceutically acceptable carriers. Non-pharmaceutical grade water is specifically included in these non-pharmaceutical carriers.

The N-dodecyl heterocyclic compounds used in the present invention can also be used in a method for inhibiting the formation of slime in an aqueous system susceptible to slime formation which comprises the step of contacting the aqueous system with an N-dodecyl heterocyclic compound in an amount effective to prevent the formation of slime. The N-dodecyl heterocyclic compound may be added directly to the system under working conditions. These compounds can be used to kill slime forming organisms, both bacteria and fungi. This method is effective in aqueous liquids such as a pulp slurry for use in papermaking or liquids contained in a water cooling device.

A further use of the compounds in the present invention resides in a method of inhibiting microbiological deterioration or disfigurement comprising the step of contacting a substance susceptible to microbiological deterioration or disfigurement with an N-dodecyl heterocyclic compound in an amount effective to inhibit the growth of microorganisms. These microorganisms include fungi. The N-dodecyl heterocyclic compound may be applied to the substance or admixed with the components which make up the substance. This method is effective on substances such as wood, paint-film, leather, flexible plastic, textiles and the like. In the preservation of leather, these compounds can be absorbed onto the hides and thus can be used in the long term preservation of leather. Similarly, in wood preservation applications, the N-dodecyl heterocyclic compounds provide a method for inhibiting the growth of wood-decaying organisms over a short or long period of time.

The compounds used in accordance with the present invention have a number of advantages over other known microbicides. They are excellent microbicides to be used for both preservation of paint while in the can and after application on the painted surface. They are hydrolytically stable over a wide pH range (3–11) and can be used in both latex and oil-based systems. They are soluble in many solvents, and may therefore be readily diluted for convenience of use. Their compatibility, low color, and efficiency makes them advantageous for use as a microbicide in plastic, and for impregnation in or application on the surface of wood, paper, cloth or other materials.

The N-dodecyl heterocyclic compounds may be applied in various ways or incorporated into a coating or composition, applied as dust by mixing with powdered diluents, dissolved in a solvent, or emulsified into water and then dispersed into a non-solvent. One of ordinary skill would therefore recognize that the particular application desired will generally dictate the method of use.

The effective amount or percentage of active compounds necessary to achieve the desired result will vary somewhat depending on the substrate or aqueous system to be protected, the conditions for microbial growth, and the degree of protection desired. The concentration of the compounds of the present invention generally ranges from about 0.0001% to 4% (w/w); preferably 0.0001% to 0.2%, and more preferably 0.0005% to 0.0050% in the composition applied. One of ordinary skill can readily determine the effective amount required for a particular application by simply testing various concentrations prior to treatment of the entire effected substrate or system.

With aqueous systems, a preferred effective amount of active compound ranges from about 20 to 5000 parts per million, and more preferably, from about 250 to 2000 parts per million of the aqueous system. The amount of N-Dodecyl heterocyclic compound effective to prevent the formation of slime in an aqueous liquid preferably ranges from about 1 to 200 parts per million, and more preferably, from about 1 to 25 parts per million of the aqueous liquid.

The following examples are given to illustrate the nature of the invention. It should be understood, however, that the invention is not to be limited to the specific conditions or details set forth in these examples.

EXAMPLE 1

Preparation of N-Dodecylmorpholine (Compound 1)

174.2 g of morpholine (1 mole), 69 g of potassium carbonate (0.5 mole) and 300 mL of acetone were heated to reflux. To the above solution 124.5 g (0.5 mole) of dodecylbromide were added dropwise. After the addition was complete, the reaction mixture was heated at reflux for four hours. The reaction mixture was filtered, and the solvent evaporated in vacuo to leave an oil, which was distilled under vacuum to give a colorless liquid. Yield is 112.9 g (90% of the theory). Proton NMR $\delta$0.8 (S,3Hz) 1.2 (M, 22Hz), 2.3 (M,4Hz) and 3.5 (M,4Hz). Elemental analysis, observed (theory) is carbon 74.96 (75.25), hydrogen 13.21 (13.02), and nitrogen 5.38 (5.48). Close proximity between the observed and theoretical values indicates the positive identification of this compound. Similarly prepared compounds are shown in Table I:

TABLE I

| COMPOUND | PROTON NMR ($\delta$) DATA* |
|---|---|
| 2. N-Dodecylimidazole | 0.8(S, 3Hz) 1.2(M, 22Hz) 7.1(D, 2Hz) 7.7(S, 1Hz) |
| 3. N-Dodecyl-2,6-dimethyl morpholine | 0.8(S, 3Hz) 1.1(M, 6Hz) 1.2(M, 22Hz) 2.6(M, 4Hz) 3.6(M, 2Hz) |
| 4. N-Dodecyl-5-chloromethyl-2-oxazolidinone | 0.8(S, 3Hz) 1.2(M, 22Hz) 3.4(M, 2Hz) 3.7(M, 2Hz) 4.8(M, 1Hz) |
| 5. N-Dodecyl-2-pyrrolidinone | 0.8(S, 3Hz) 1.2(M, 22Hz) 2.2(M, 4Hz) 3.4(M, 2Hz) |
| 6. N-Dodecylhexamethyleneimine | 0.8(S, 3Hz) 1.2(M, 22Hz) 1.6(S, 8Hz) 2.8(M, 4Hz) |
| 7. N-Dodecylpyrrolidine | 0.8(S, 3Hz) 1.2(M, 22Hz) 1.7(M, 4Hz) 2.4(M, 4Hz) |
| 8. N-Dodecyl-3-methyl piperidine | 0.8(S, 3Hz) 0.9(D, 3Hz) 1.2(M, 22Hz) 1.7(M, 4Hz) 2.4(M, 1Hz) 3.0(M, 4Hz) |
| 9. N-Dodecylpiperidine | 0.8(S, 3Hz) 1.2(M, 22Hz) 1.5(M, 6Hz) 2.8(M, 4Hz) |
| 10. N-Dodecyl-4-methylpiperidine | 0.8(S, 3Hz) 0.9(S, 3Hz) 1.2(M, 22Hz) 2.2(M, 5Hz) 2.8(M, 4Hz) |
| 11. N-Dodecyl-2-methylpiperidine | 0.8(S, 3Hz) 1.1(D, 3Hz) 1.3(M, 22Hz) 1.5(M, 6Hz) 2.8(M, 3Hz) |

*Chemical Shifts in PPM, Solvent: CDCl$_3$

EXAMPLE 2

The preferred compounds of the present invention were tested by the pulp substrate method and basal salts method described in U.S. Pat. No. 2,881,070 at column 5, beginning at line 12 and extending to column 6, line 53. The disclosure of U.S. Pat. No. 2,881,070 is specifically incorporated by reference herein. As set forth therein, a percentage kill of 80% or higher represents an extremely useful microbicidal composition, but it does not follow that higher kills are necessarily better or more desirable. The minimum inhibitory concentrations are those in which a percentage kill of at least 80% is obtained. The results are presented in Table II.

TABLE II

| | Minimum inhibitory concentration Organism/Substrate | | | |
|---|---|---|---|---|
| | E. aerogenes/ Pulp Substrate | | P. aeruginosa/ Basal Salts Solution | |
| Compound | pH 6.0 | pH 8.0 | pH 6.0 | pH 8.0 |
| 1 | 25 | 25 | 8 | 40 |
| 2 | 1000 | >1000 | 4 | 10 |
| 3 | 1000 | 1000 | | |
| 4 | 1000 | 1000 | | |
| 5 | 1000 | 1000 | | |
| 6 | >1000 | 1000 | | |
| 7 | 1000 | >1000 | | |
| 8 | 1000 | >1000 | | |
| 9 | 1000 | 1000 | | |
| 10 | 100 | >1000 | | |
| 11 | 100 | >1000 | | |

EXAMPLE 3

The microorganism growth inhibiting activity of N-dodecyl heterocyclic compounds on the fungus *Aspergillus niger* was evaluated. The method is described in U.S. Pat. No. 4,945,109, column 5 beginning at line 47 to column 6, line 33. The disclosure of U.S. Pat. No. 4,945,109 is incorporated herein by reference. The minimum inhibitory concentrations are those that completely prevented the growth of fungi. The results are presented in Table III.

TABLE III

Minimum inhibitory concentration of N-dodecyl heterocyclic compounds against fungi in parts per million

| Compound | *Aspergillus niger* pH 6.0 |
|---|---|
| 1 | >100 |
| 2 | 32 |
| 3 | 128 |
| 4 | >512 |
| 5 | 32 |
| 6 | 256 |
| 7 | 128 |
| 8 | 256 |
| 9 | 32 |
| 10 | 1000 |
| 11 | 1000 |

EXAMPLE 4

The growth inhibiting activity of the method of the invention against the three algae *Chlorella pyrenoidosa*, *Chlorococcum hypnosporum* and *Phormidium inundatum* was evaluated in Difco Algae Broth, the content of which was as follows:

| Compound | Grams per liter |
|---|---|
| Sodium nitrate | 1.000 |
| Ammonium chloride | 0.050 |
| Calcium chloride | 0.058 |
| Magnesium sulfate | 0.513 |
| Dipotassium Phosphate | 0.250 |
| Ferric chloride | 0.003 |

Forty-gram portions of the algae medium were added to 250 mL Pyrex Erlenmeyer flasks fitted with loose metal caps and then sterilized. Each of the following substances wa then added to the flasks in the order listed:

1. Sterile algae medium as required to bring the total weight of the contents of each flask to 50 grams, after allowing for all subsequent additions specified below.

2. A solution of the N-dodecyl heterocyclic toxicant or of a control agent to be evaluated in each test, to give the concentration desired in parts per million by weight.

3. *Chlorella pyrenoidosa*, *Chlorococcum hypnosporum* and *Phormidium inundatum* in amounts sufficient to give excellent growth in the controls after 14 days. This was achieved by adding 1 milliliter of a 14 day old culture having luxuriant growth. The *Chlorella pyrenoidosa* culture was obtained from American Type Culture Collection No. 7516; *Chlorococcum hynosporum*, from the University of Texas at Austin; and *Phormidium inundatum*, Wisconsin No. 1093, from the University of Washington.

As a control experiment, WSCP was used as a positive control agent. WSCP is a known toxicant which kills *C. pyrenoidosa* at 2 ppm, *C. hypnosporum* at 2 ppm and *P. inundatum* at 10 ppm. Control experiments were also carried out where no toxicants were also employed. In the algicidal tests the growth of algae in the nutrient medium is lush green and can be seen with the naked eye. Because the minimum inhibitory concentrations of the compounds in this example are those which result in complete inhibition evaluation of the test results is not subjective.

After the inoculum of the test algae was added, the flasks were incubated at a temperature of 28° ±2° C. under fluorescent illumination of 250 foot-candle intensity (8 hours light, 16 hours darkness) for a period adequate for growth in the controls (those portions of medium which contained no toxicant). Observations of growth were made at 7-day intervals. Minimum inhibitory concentrations are those that prevented complete growth after 28 days. The results are summarized in Table IV.

TABLE IV

Minimum inhibitory concentration of N-dodecyl heterocyclic compounds against algae in parts per million

| Compound | *C. pyrenoidosa* pH 7.0 | *C. hypnosporum* pH 7.0 | *P. inundatum* pH 7.0 |
|---|---|---|---|
| 1 | 1 | 1 | — |
| 2 | 0.5 | 0.7 | 2.0 |
| 3 | 10 | <1 | 1000 |
| 4 | 100 | 100 | 100 |
| 5 | 10 | 10 | 10 |
| 6 | 1 | 1 | 10 |
| 7 | 1 | 1 | 1 |
| 8 | 10 | 1 | 10 |
| 9 | 1 | 1 | 10 |
| 10 | <1 | <1 | <1 |
| 11 | <1 | <1 | 5 |

The claimed invention is:

1. A method for inhibiting the growth of at least one microorganism in an industrial aqueous system, said system being susceptible to the growth of a microorganism, comprising the step of contacting said industrial aqueous system with an N-dodecyl heterocyclic compound having the following general formula:

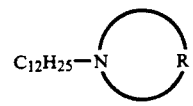

wherein the heterocyclic ring defined by

is a substituted or unsubstituted group selected from pyrrolidinyl, 2-pyrrolidinonyl, pyrrollinyl, pyrazolidinyl, pyrazolinyl, pyrazolyl, imidizolidinyl, imidizolinyl, imidazolyl, oxazolinyl, piperadinyl, piperazinyl, morpholinyl, hexamethyleneimine or heptamethyleneimine, in an amount effective to inhibit the growth of said microorganism.

2. The method of claim 1 wherein said aqueous system is an aqueous-based solution, an aqueous-based emulsion or an aqueous-based suspension.

3. The method of claim 2 wherein said aqueous-based emulsion is a paint.

4. The method of claim 2 wherein said aqueous-based solution is a metalworking fluid.

5. The method of claim 1 wherein said N-dodecyl heterocyclic compound is selected from the group of N-dodecylmorpholine, N-dodecylimidazole, N-dodecyl-2,6-dimethylmorpholine, N-dodecyl-5-chloromethyl-2-oxazolidinone, N-dodecyl-2-pyrrolidino N-dodecylhexamethyleneimine, N-dodecylpyrrolidine, N-dodecyl-3-methylpiperidine, N-dodecylpiperidine, N-dodecyl-4-methylpiperidine and N-dodecyl-2-methylpiperidine.

6. The method of claim 5 wherein the N-dodecyl heterocyclic compound is N-dodecylmorpholine or N-dodecylimidazole.

7. The method of claim 1 wherein said effective amount is from about 20 to about 5000 ppm of said aqueous system.

8. The method of claim 7 wherein said effective amount is from about 250 to about 2000 ppm of said aqueous system.

9. The method of claim 1, wherein said aqueous system is selected from pulp and paper systems, industrial cooling water and water-based paints.

10. A method according to claim 1 wherein the pH of the aqueous system is 7-11.

11. A method according to claim 1 wherein the pH of the aqueous system is 3-11.

12. A method of inhibiting the formation of slime comprising the step of contacting an industrial aqueous system susceptible to the formation of slime with an N-dodecyl heterocyclic compound having the following general formula:

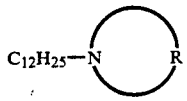

wherein the heterocyclic ring defined by

is a substituted or unsubstituted group selected from pyrrolidinyl, 2-pyrrolidinoyl, pyrrollinyl, pyrazolidinyl, pyrazolinyl, pryrazolyl, imidizolidinyl, imidizolinyl, imidazolyl, oxazolinyl, piperadinyl, piperazinyl, morpholinyl, hexamethyleneimine or heptamethyleneimine, in an amount effective to inhibit the formation of said slime.

13. The method of claim 12 wherein said effective amount is from about 1 to 200 ppm of said aqueous system.

14. The method of claim 13 wherein said effective amount is from about 5 to about 25 ppm of said aqueous system.

15. The method of claim 12 wherein said aqueous system is a pulp slurry.

16. The method of claim 12 wherein said aqueous system is contained in a water cooling device.

17. The method of claim 12 wherein said N-dodecyl heterocyclic compound is selected from the group of N-dodecylmorpholine, N-dodecylimidazole, N-dodecyl-2,6-dimethylmorpholine, N-dodecyl-5-chloromethyl-2-oxazolidinone, N-dodecyl-2-pyrrolidinone, N-dodecylhexamethyleneimine, N-dodecylpyrrolidine, N-dodecyl-3-methylpiperidine, N-dodecylpiperidine, N-dodecyl-4-methylpiperidine and N-dodecyl-2-methylpiperidine.

18. The method of claim 17 wherein the N-dodecyl heterocyclic compound is N-dodecylmorpholine or N-dodecylimidazole.

19. The method of claim 12, wherein said aqueous system is selected from pulp and paper systems, industrial cooling water and water-based paints.

20. A method of inhibiting microbiological deterioration of disfigurement comprising the step of contacting a substance susceptible to microbiological deterioration or disfigurement with an N-dodecyl heterocyclic compound having the following general formula:

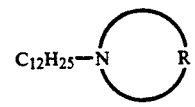

wherein the heterocyclic ring defined by

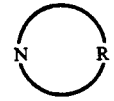

is a substituted or unsubstituted group selected from pyrrolidinyl, 2-pyrrolidinonyl, pyrrollinyl, pyrazolidinyl, pyrazolinyl, pyrazolyl, imidizolidinyl, imidizolinyl, imidazolyl, oxazolinyl, piperiadinyl, piperazinyl, morpholinyl, hexamethyleneimine or heptamethyleneimine, in an amount effective to inhibit the growth of at least one microorganism, wherein said substance is selected from the group consisting of wood, paint-film, leather, flexible plastic, and textiles.

21. The method of claim 20 wherein said contacting step is a step of applying said N-dodecyl heterocyclic compound to said substance.

22. The method of claim 20 wherein said contacting step is a step of admixing said N-dodecyl heterocyclic compound with the components which constitute the surface of said substance.

23. The method of claim 20 wherein said N-dodecyl heterocyclic compound is selected from the group of N-dodecylmorpholine, N-dodecylimidazole, N-dodecyl-2,6-dimethylmorpholine, N-dodecyl-5-chloromethyl-2-oxazolidinone, N-dodecyl-2-pyrrolidinone, N-dodecylhexamethyleneimine, N-dodecylpyrrolidine, N-dodecyl-3-methylpiperidine, N-dodecylpiperidine, N-dodecyl-4-methylpiperidine and N-dodecyl-2-methylpiperidine.

24. The method of claim 23 wherein the N-dodecyl heterocyclic compound is N-dodecylmorpholine or N-dodecylimidazole.

25. The method of claim 20 wherein said at least one microorganism is a fungus.

* * * * *

UNITED STATES PATENT AND TRADEMARK OFFICE
CERTIFICATE OF CORRECTION

PATENT NO. : 5,250,194
DATED : October 5, 1993
INVENTOR(S) : C. George Hollis et al.

It is certified that error appears in the above-indentified patent and that said Letters Patent is hereby corrected as shown below:

IN THE CLAIMS:

Claim 5, Column 9, line 5, "N-dodecyl-2-pyrrolidino" should read --N-dodecyl-2-pyrrolidinone,--.

Claim 12, Column 9, line 46, "2-pyrrolidinoyl" should read --2-pyrrolidinonyl--.

Claim 13, Column 9, line 53, before "200" insert --about--.

Claim 17, Column 10, line 2, "5" should read --5--.

Claim 20, Column 10, line 15, "of" (first occurrence) should read --or--; and

Claim 20, Column 10, line 36, "piperiadinyl" should read --piperadinyl--.

UNITED STATES PATENT AND TRADEMARK OFFICE
CERTIFICATE OF CORRECTION

PATENT NO.   : 5,250,194
DATED        : October 5, 1993
INVENTOR(S)  : C. George Hollis et al.

It is certified that error appears in the above-indentified patent and that said Letters Patent is hereby corrected as shown below:

Col. 10, line 35, "pyrazolyl" should read --pryrazolyl--.

Signed and Sealed this

Nineteenth Day of April, 1994

Attest:

BRUCE LEHMAN

*Attesting Officer*            *Commissioner of Patents and Trademarks*